(12) United States Patent
Baumgart et al.

(10) Patent No.: US 10,064,595 B2
(45) Date of Patent: Sep. 4, 2018

(54) SYSTEM FOR COREGISTRATION OF OPTICAL COHERENCE TOMOGRAPHY AND ANGIOGRAPHIC X-RAY IMAGE DATA

(71) Applicants: John Baumgart, Hoffman Estates, IL (US); Olivier Ecabert, Pretzfeld (DE); John Christopher Rauch, Warwick, RI (US)

(72) Inventors: John Baumgart, Hoffman Estates, IL (US); Olivier Ecabert, Pretzfeld (DE); John Christopher Rauch, Warwick, RI (US)

(73) Assignee: Siemens Healthcare GmbH, Erlangen (DE)

( * ) Notice: Subject to any disclaimer, the term of this patent is extended or adjusted under 35 U.S.C. 154(b) by 642 days.

(21) Appl. No.: 13/856,510

(22) Filed: Apr. 4, 2013

(65) Prior Publication Data
US 2013/0281832 A1 Oct. 24, 2013

Related U.S. Application Data

(60) Provisional application No. 61/637,359, filed on Apr. 24, 2012.

(51) Int. Cl.
*A61B 5/05* (2006.01)
*A61B 6/00* (2006.01)
*A61B 5/00* (2006.01)
*A61B 6/12* (2006.01)
(Continued)

(52) U.S. Cl.
CPC .......... *A61B 6/5247* (2013.01); *A61B 5/0035* (2013.01); *A61B 5/0066* (2013.01); *A61B 5/0084* (2013.01); *A61B 5/4839* (2013.01); *A61B 5/7289* (2013.01); *A61B 6/12* (2013.01); *A61B 6/4417* (2013.01); *A61B 6/4441* (2013.01); *A61B 6/484* (2013.01); *A61B 6/503* (2013.01); *A61B 6/504* (2013.01); *A61B 6/541* (2013.01); *A61B 5/0452* (2013.01); *A61M 5/007* (2013.01)

(58) Field of Classification Search
USPC ........ 600/407, 424–428, 462, 466–467, 476, 600/478
See application file for complete search history.

(56) References Cited

U.S. PATENT DOCUMENTS

| | | |
|---|---|---|
| 7,657,069 B2 | 2/2010 | Boese et al. |
| 7,930,014 B2 | 4/2011 | Huennekens et al. |
| 2004/0097805 A1 | 5/2004 | Verard et al. |

(Continued)

*Primary Examiner* — James Kish

(57) ABSTRACT

A system comprises a catheter including a lens, for acquiring optical coherence tomography images within the vessel of interest as the catheter is being retracted from the vessel in the presence of contrast agent. An X-ray imaging system interface receives a first set of X-ray images of an anatomical region including the vessel of interest containing the catheter. The first set of X-ray images are acquired at points corresponding to the particular points within a heart cycle, while the catheter is stationary in the vessel, in response to a heart electrical activity representative signal and in the absence of contrast agent. An image data processor associates the received X-ray images and corresponding optical coherence tomography image data derived at corresponding time points within respective acquisition heart cycles.

13 Claims, 5 Drawing Sheets

(51) Int. Cl.
    *A61M 5/00*    (2006.01)
    *A61B 5/0452*    (2006.01)

(56) References Cited

U.S. PATENT DOCUMENTS

| | | |
|---|---|---|
| 2007/0123771 A1* | 5/2007 | Redel et al. .................. 600/407 |
| 2007/0276216 A1* | 11/2007 | Beyar et al. .................. 600/407 |
| 2009/0177050 A1 | 7/2009 | Griffiths et al. |
| 2009/0192358 A1 | 7/2009 | Jaffer et al. |
| 2010/0094124 A1* | 4/2010 | Schoonenberg et al. ..... 600/424 |
| 2010/0210938 A1 | 8/2010 | Verard et al. |
| 2011/0306867 A1 | 12/2011 | Gopinathan et al. |
| 2012/0059249 A1 | 3/2012 | Verard et al. |
| 2012/0063570 A1* | 3/2012 | Furuichi et al. ............. 378/98.2 |
| 2012/0101369 A1 | 4/2012 | Patil et al. |
| 2013/0216114 A1* | 8/2013 | Courtney ............. A61B 5/0066 382/130 |

\* cited by examiner

SYSTEM FOR COREGISTRATION OF OPTICAL COHERENCE TOMOGRAPHY AND ANGIOGRAPHIC X-RAY IMAGE DATA

This is a non-provisional application of provisional application Ser. No. 61/637,359 filed Apr. 24, 2012, by J. Baumgart et al.

FIELD OF THE INVENTION

This invention concerns a system for associating optical coherence tomography image data with X-ray image data at corresponding time points within respective acquisition heart cycles.

BACKGROUND OF THE INVENTION

Co-registration of optical coherence tomography (OCT) pullback image data and an angiographic X-ray image involves different problems than are involved in other types of pullback imaging registration such as IVUS (intra-vascular ultra sound) and angiography image registration. Since an IVUS pullback is performed without the injection of contrast agent into vessels, it is possible to image an IVUS catheter with X-ray during catheter pullback. OCT, however, requires contrast medium for its imaging, making the vessels radio-opaque and effectively hiding the catheter. An IVUS pullback is also performed slowly over a period of 1 to 3 minutes, allowing the catheter to be imaged multiple times such that each image of the catheter can be made at the same time within a heart cycle, thus substantially eliminating the effect of cardiac motion that distorts the shape of a catheter in a vessel being imaged. An OCT pullback is performed quickly, usually in less than 3 seconds. Even if it is possible to image an OCT catheter during the pullback, ECG-gated imaging of the catheter would only produce 2 or 3 frames. A system according to invention principles addresses these deficiencies and associated problems.

SUMMARY OF THE INVENTION

A system produces co-registered optical coherence tomography (OCT) pullback image data and angiographic X-ray image data with minimal user interaction. A system associates optical coherence tomography image data with X-ray image data. The system comprises a catheter including a lens, for acquiring optical coherence tomography images within the vessel of interest as the catheter is being retracted in the presence of contrast agent. An X-ray imaging system interface receives a first set of X-ray images of an anatomical region including the vessel of interest containing the catheter. The first set of X-ray images are acquired at points corresponding to the particular time points within a heart cycle, while the catheter is stationary in the vessel, in response to a heart electrical activity representative signal and in the absence of contrast agent. An image data processor associates the received X-ray images and corresponding optical coherence tomography image data derived at corresponding time points within respective acquisition heart cycles.

DETAILED DESCRIPTION OF THE INVENTION

A system acquires images for an angiography system to determine a shape, and thus the trajectory, of an OCT catheter during one or more specific points in a cardiac cycle. The system acquires sufficient contrast-filled images to document a time duration encompassing injection of contrast agent for an OCT pullback, including multiple contrast agent-filled images acquired at the same particular point within a cardiac cycle as images acquired of an OCT catheter without the presence of contrast agent. The system acquires additional images showing retraction of an OCT catheter in a pullback path without the presence of contrast agent but acquired at same point of the cardiac cycle as the initial frames acquired of the shape of the catheter before the pullback, thus enabling the path to be seen by X-ray and be analyzed to determine catheter trajectory.

Figure 1:
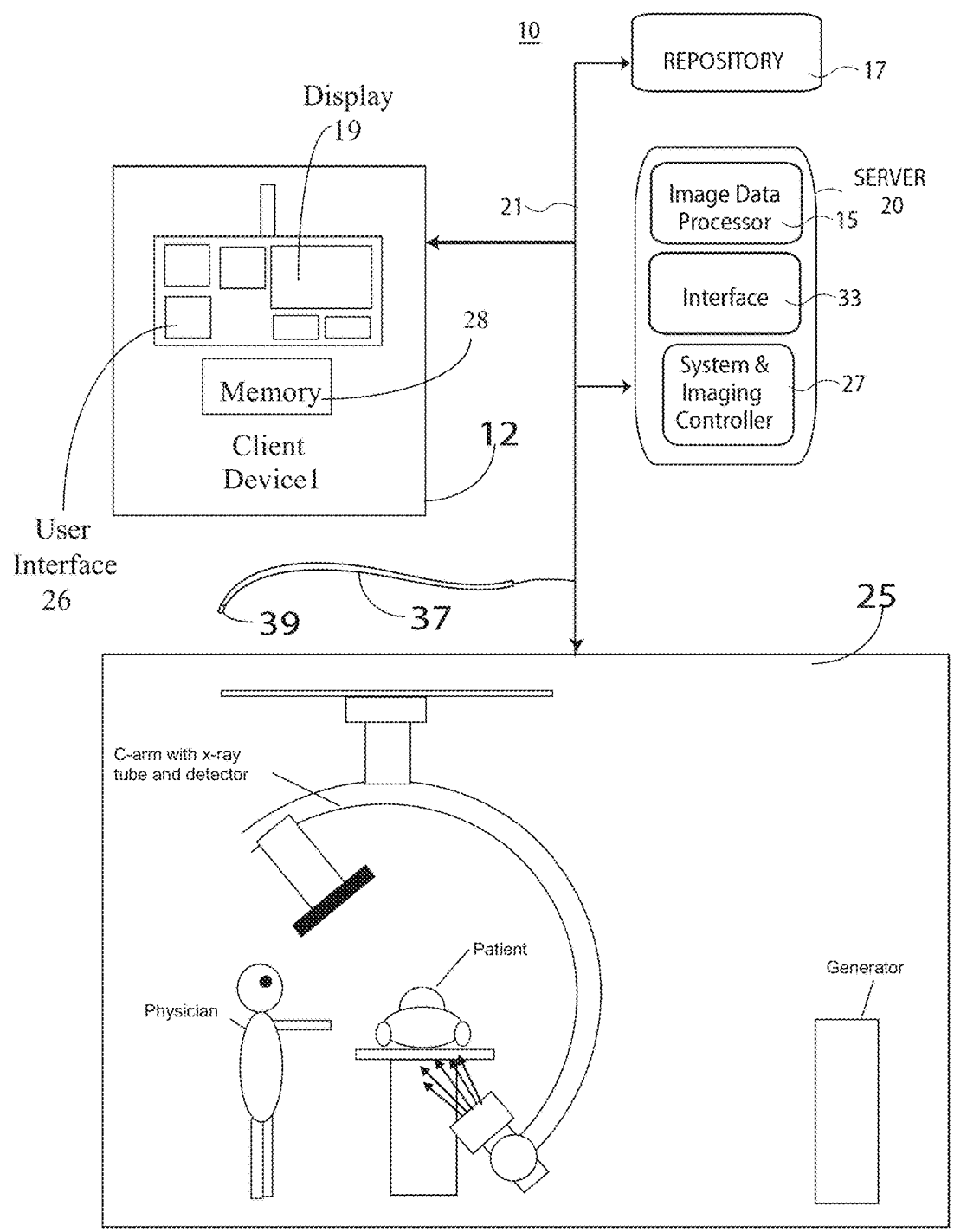
FIG. 1 shows a system for associating optical coherence tomography image data with X-ray image data, according to invention principles.

FIG. 1 shows system 10 for associating optical coherence tomography image data with X-ray image data. System 10 includes one or more processing devices (e.g., workstations, computers or portable devices such as notebooks, Personal Digital Assistants, phones) 12 that individually include memory 28, a user interface 26 enabling user interaction with a Graphical User Interface (GUI) and display 19 supporting GUI and medical image presentation in response to predetermined user (e.g., physician) specific preferences. System 10 also includes at least one repository 17, server 20 and catheter 37 having lens 39 and imaging device 25. Server 20 includes image data processor 15, interface 33 and system and imaging control unit 27. System and imaging control unit 27 controls operation of catheter 37 for performing optical coherence tomography (OCT) pullback image data acquisition and controls imaging device 25 for performing image acquisition of patient anatomy in response to user command. Imaging devices 25 may comprise a mono-plane or biplane X-ray imaging system. The units of system 10 intercommunicate via network 21. At least one repository 17 stores OCT pullback image data and X-ray medical images and studies for patients in DICOM compatible (or other) data format. A medical image study individually includes multiple image series of a patient anatomical portion which in turn individually include multiple images.

Figure 2:
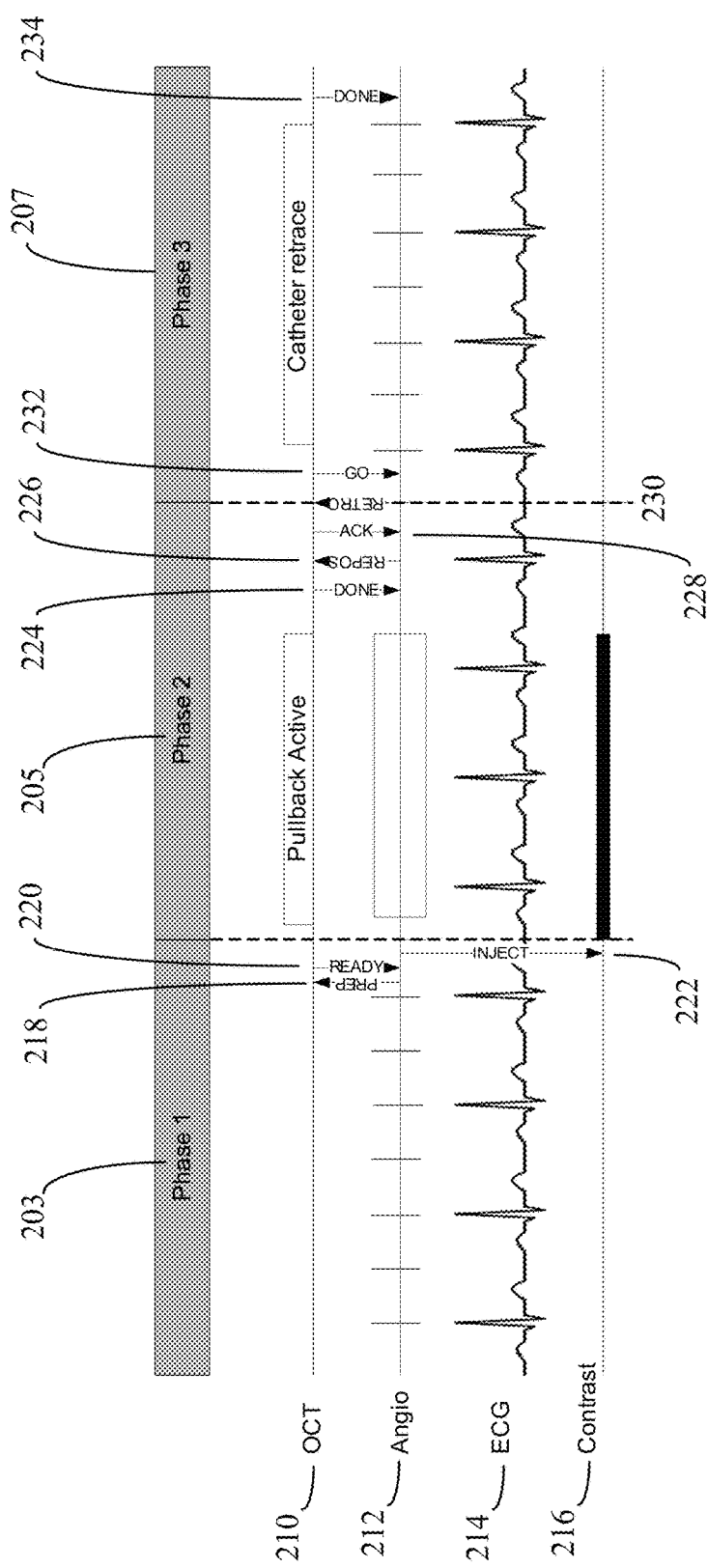
FIG. 2 shows synchronization of an X-ray angiography system, an OCT system, and contrast agent injection, and a patient ECG waveform, according to invention principles.

Catheter 37 includes lens 39 and acquires optical coherence tomography images within a vessel of interest at particular points within a heart cycle as catheter 37 is being retracted from the vessel in the presence of contrast agent. X-ray imaging system interface 33 receives a first set of X-ray images of an anatomical region including the vessel of interest containing the catheter from imaging system 25. The first set of X-ray images are acquired at points corresponding to the particular points within a heart cycle, while the catheter is stationary in the vessel, in response to a heart electrical activity representative signal and in the absence of contrast agent. Image data processor 15 associates the received X-ray images and corresponding optical coherence tomography image data derived at corresponding time points within respective acquisition heart cycles. X-ray imaging system interface 33 receives a second set of X-ray images of an anatomical region including the vessel of interest in the absence of contrast agent as catheter 37 is being reinserted retracing the retraction path. Catheter 37 initiates acquisition of the optical coherence tomography images and retraction from the vessel in response to a signal associated with completion of acquisition of the first set of X-ray images FIG. 2 shows a timeline (time on horizontal axis) of synchronization between an X-ray angiography system, an OCT system, and contrast agent injection and a patient ECG waveform. The image acquisition process comprises phase 1, 203, phase 2, 205 and phase 3, 207. X-ray imaging system 25 (FIG. 1) acquires X-ray images in phase 1 203 as indicated in X-ray acquisition pulse sequence 212 in response to an ECG signal 214 trigger. An individual frame is acquired in response to the ECG trigger and optional additional frames are acquired corresponding to a fixed predetermined offset from the trigger. The shape of catheter 37 is ascertained by image data processor 15 by analysis of images acquired at points of a cardiac cycle using known feature segmentation methods. Specifically, by object edge identification using pixel luminance transition detection and matching with template object shapes using iterative rotation, translation and scaling operations, for example. Object detection is performed by object edge detection using a known edge detection function based on adjacent pixel luminance transition occurrence and by object shape matching and comparison with template features (e.g. spaced bands) using scaling, rotation and translation operations.

In response to acquisition of X-ray images showing the catheter shape and trajectory, system 10 transitions to an OCT pullback phase 2, 205. This transition is triggered automatically by processor 15 of system 10 after catheter shape has been determined, or is triggered by a user manually triggering the transition (using, for example, an X-ray switch or a dedicated manual trigger device). In response to triggering of a pullback phase, processor 15 notifies the OCT system controller 27 (PREP signal 218 in timeline) and awaits confirmation (READY signal 220) that it is ready to perform the pullback. X-ray system 25 initiates acquisition of X-ray images for the pullback phase and requests that contrast agent be injected (INJECT signal 222) in order for initiation of OCT system image data acquisition. The contrast agent injection request may comprise an automatic trigger of a contrast agent injector or a prompt message communicated to a worker (e.g. via display 19) to manually perform the injection. Contrast agent injection time line 216 shows injection duration in phase 2 205.

Processor 15 automatically (or in response to manual interaction in one embodiment) selects X-ray images indicating catheter shape. Specifically, processor 15 automatically selects X-ray images acquired during the pullback phase, one for each shape, such that they are from the same part of the cardiac cycle and are representative of a peak contrast agent concentration for available images at that point of the cardiac cycle. This results in a pair of images for each point in the cardiac cycle that is being sampled, where one image is an X-ray image showing shape of the catheter and one is an OCT image showing internal vasculature. OCT time line 210 shows catheter 37 pullback and pullback retracement periods. Processor 15 uses the catheter shape to track the corresponding vessel in the contrast image, giving a map of the vessel for each point in the cardiac cycle that was sampled. To trigger the end of the second phase, the X-ray system awaits a signal from the OCT system that its pullback has finished (DONE signal 224). Alternatively, a manual trigger can be used.

Processor 15 initiates phase 3, 207 in response to processor 15 requesting that the OCT system reposition catheter 37 such that it can retrace the path of the pullback (REPOS signal 226), and waits for the OCT system to signal that it is ready (ACK signal 228). In response to controller 27 receiving signal 228, X-ray imaging system 25 initiates acquisition of X-ray images and signals the OCT system to begin retracing the pullback at a slower rate (RETRC signal 230), thus allowing acquisition of the OCT catheter position. X-ray system 25 in phase 3 207, acquires X-ray images (GO signal 232) at the same points in the cardiac cycle as were used in phase 1 203 to acquire the shape of the catheter. As the X-ray images are acquired, processor 15 determines the location of lens 39 of OCT catheter 37 using a known previously described image analysis object detection method.

In response to pullback retracement completion, phase 3 207 is terminated by X-ray imaging system 25 receiving a signal from the OCT system (second DONE signal 234). Alternatively, a manual trigger may be used. The result of the tracking of phase 3 207 is a series of maps of the OCT lens, one map for each of the points of the cardiac cycle used in phase 1 203. Since the sequence of acquired X-ray images is known, these maps are interleaved in one embodiment to create a more accurate map of an entire vessel than may be created by using a single map.

The order of the catheter pullback and X-ray image acquisition to locate the catheter transducer is not fixed. In other embodiments, the X-ray image acquisition to locate catheter 39 transducer positions is performed either before the pullback or after the pullback (as described above). In the case of X-ray image acquisition to locate catheter 39 transducer positions being performed before the pullback, in FIG. 2, the order of the pullback and the catheter retrace phases is interchanged, the sequence starting with the RETRC 230 signal and ending with the DONE 234 signal occurs before the PREP 218 signal. Further, X-ray image acquisition to locate transducer positions occurs either during the pushback (as described above) or during a second pullback at a much slower rate. The benefit of X-ray image acquisition during a second pullback at a much slower rate is that it removes hysteresis effects occurring due to device and vessel compliance as well as the fact that the advancement path may be different than the retraction path. The larger the vessel is in relation to the catheter, the more likely it is that the advancement and retraction paths of the catheter will vary significantly.

Figure 3:
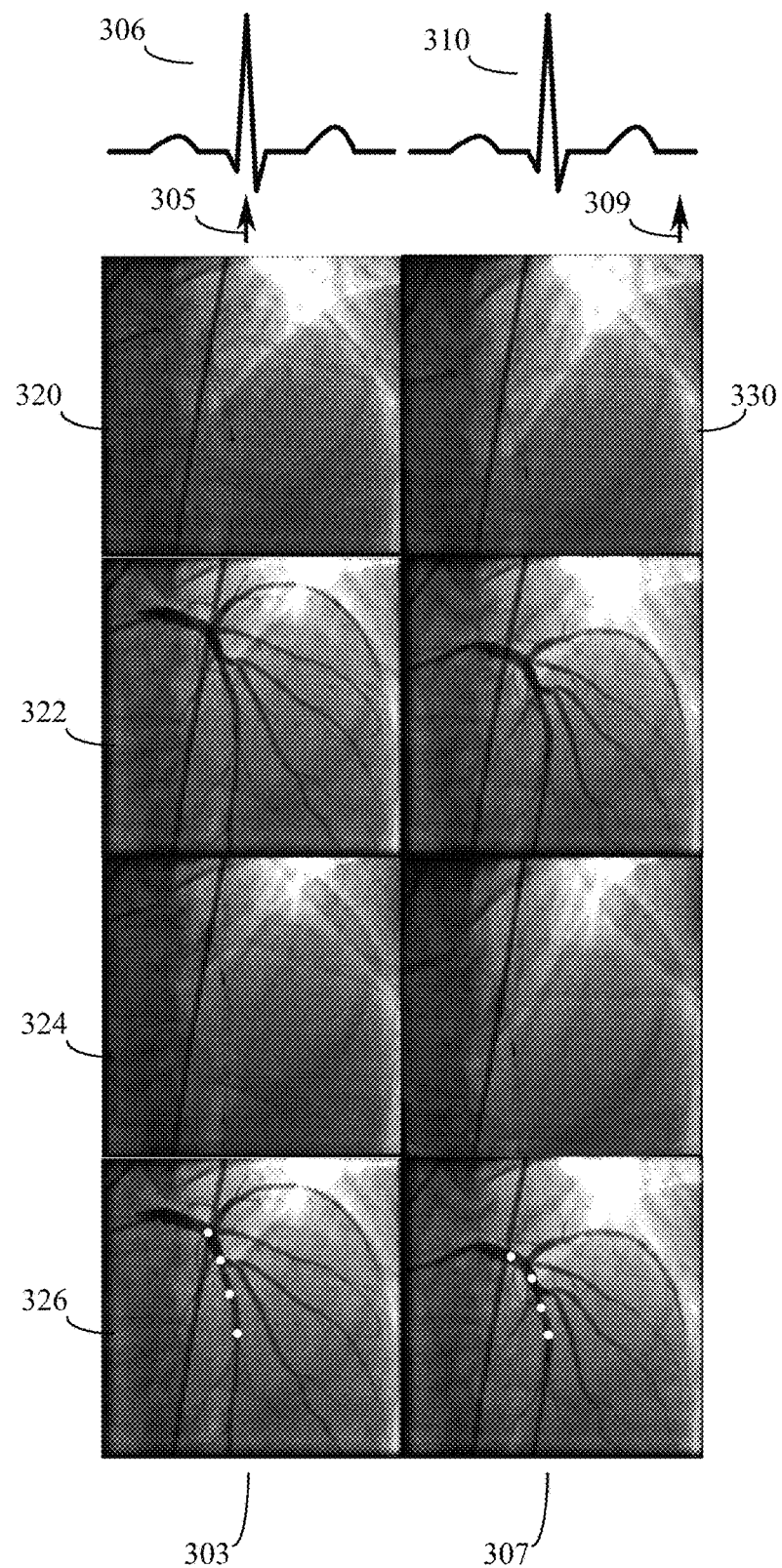
FIG. 3 shows different images acquired during different phases including one set of images for each part of a cardiac cycle that is imaged, according to invention principles.

FIG. 3 shows different images acquired by system 10 (FIG. 1) during different phases of FIG. 2 including one set of images for each part of a cardiac cycle that is imaged. Images are acquired in response to radiation pulses at the R-wave peaks 305 and half-way between the peaks 309. First set of images (column 303) comprise images acquired by imaging system 25 for point 305 in a cardiac cycle of ECG wave 306 and second set of images (column 307) comprise images acquired by imaging system 25 for point 309 of ECG wave 310. The pair of images 320, 330 represents fluoroscopy images respectively acquired during phase 1 203 (FIG. 2) at points 305, 309 in a cardiac cycle, where OCT catheter 37 is fully advanced. The tip of catheter 37 is located in a different place in image 330 than in image 320, due to cardiac motion. The pair of images on row 322 represents images acquired during contrast agent injection in phase 2 205, and shows coronary arteries and how they move and deform during a cardiac cycle. The pair of images on row 324 represents images acquired during phase 3 207, with catheter 37 retracing the pullback. The pair of images on row 326 represents points on the vessel that were mapped by images acquired during phase 3 207.

Figure 4:
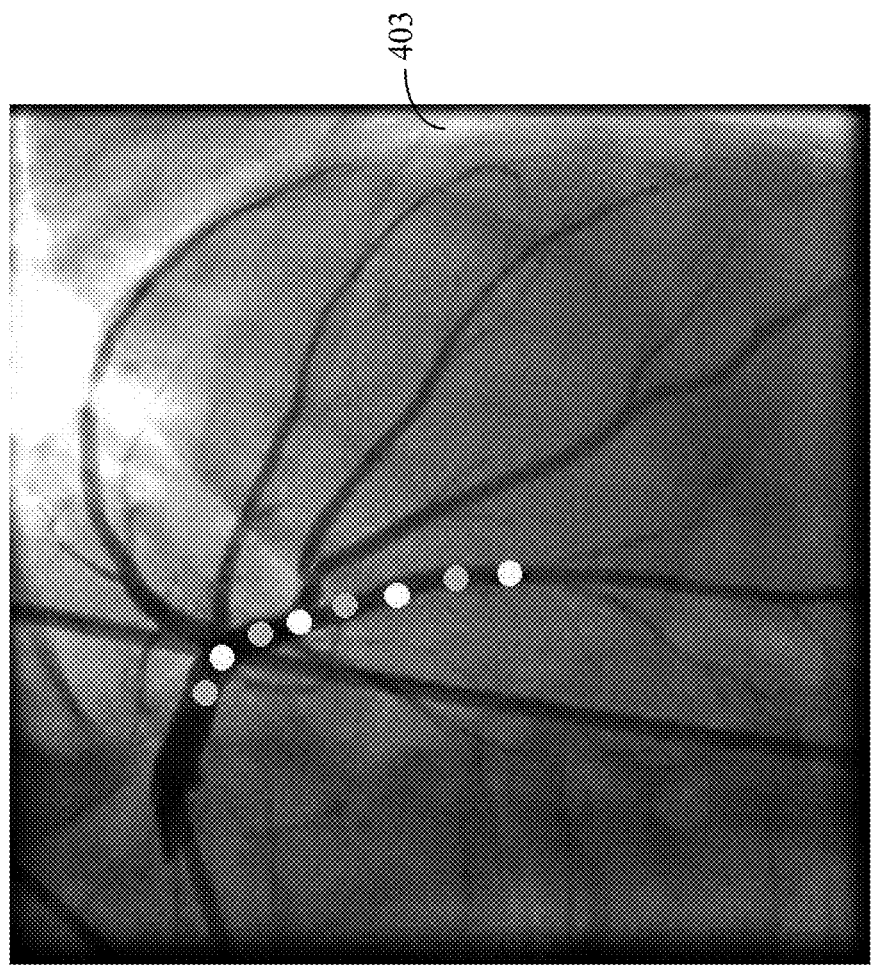
FIG. 4 shows a final map of a vessel created by merging maps for multiple points in a cardiac cycle, according to invention principles.

FIG. 4 shows final map 403 of a vessel created by merging maps for multiple points in a cardiac cycle. Vessel map 403 is created by merging maps for each point in the cardiac cycle that were mapped at the end of phase 3 207 (FIG. 2). The merged map is created by interleaving tracked points on the vessel for the varying points in the cardiac cycle based on distance from an initial position of the catheter 37 tip, which is stationary during phase 1 203, to the tracked location, along the tracked vessel. An interleaved map is generated from one or more maps, where each map represents a specific point in time in a cardiac cycle. One map is made from images acquired in response to X-ray radiation pulses that occur at an R-wave peak, and another different map is generated from images acquired using X-ray pulses that occur half-way between R-wave peaks, for example. These maps are created separately, as they represent a different picture of a beating heart. Once the maps have been created, they are interleaved with each other. The time at which each X-ray radiation pulse is emitted and each associated image is acquired is known and processor 15 links image feature positions from a map created at a half-way point between R-wave peaks to corresponding image feature positions in a map created at the R-wave peaks by interleaving them.

Processor 15 employs a known catheter detection function to track catheter 37 in an image and to identify and segment a vessel in an image containing catheter 37 when it is filled with contrast agent which obscures the catheter. Segmenting the vessel in images gives a map of points that are connected, for example, by drawing a line down the centre of the vessel. The images are of catheter 37 progressively advancing through the vessel. The detection function determines location of catheter 37 with respect to a matching phase 1 203 image of a fully advanced catheter and maps the catheter onto a segmented, contrast-filled vessel. The catheter detection function performs catheter detection by catheter edge detection using a known edge detection function based on adjacent pixel luminance transitions and by catheter shape matching and comparison with template features using iterative scaling, rotation and translation operations, for example. X-ray images are acquired using pulsed X-ray emission having a reduced time duration X-ray exposure comprising a short pulse (e.g., 15 msec) for an image frame acquisition and is not continuously turned on.

Figure 5:
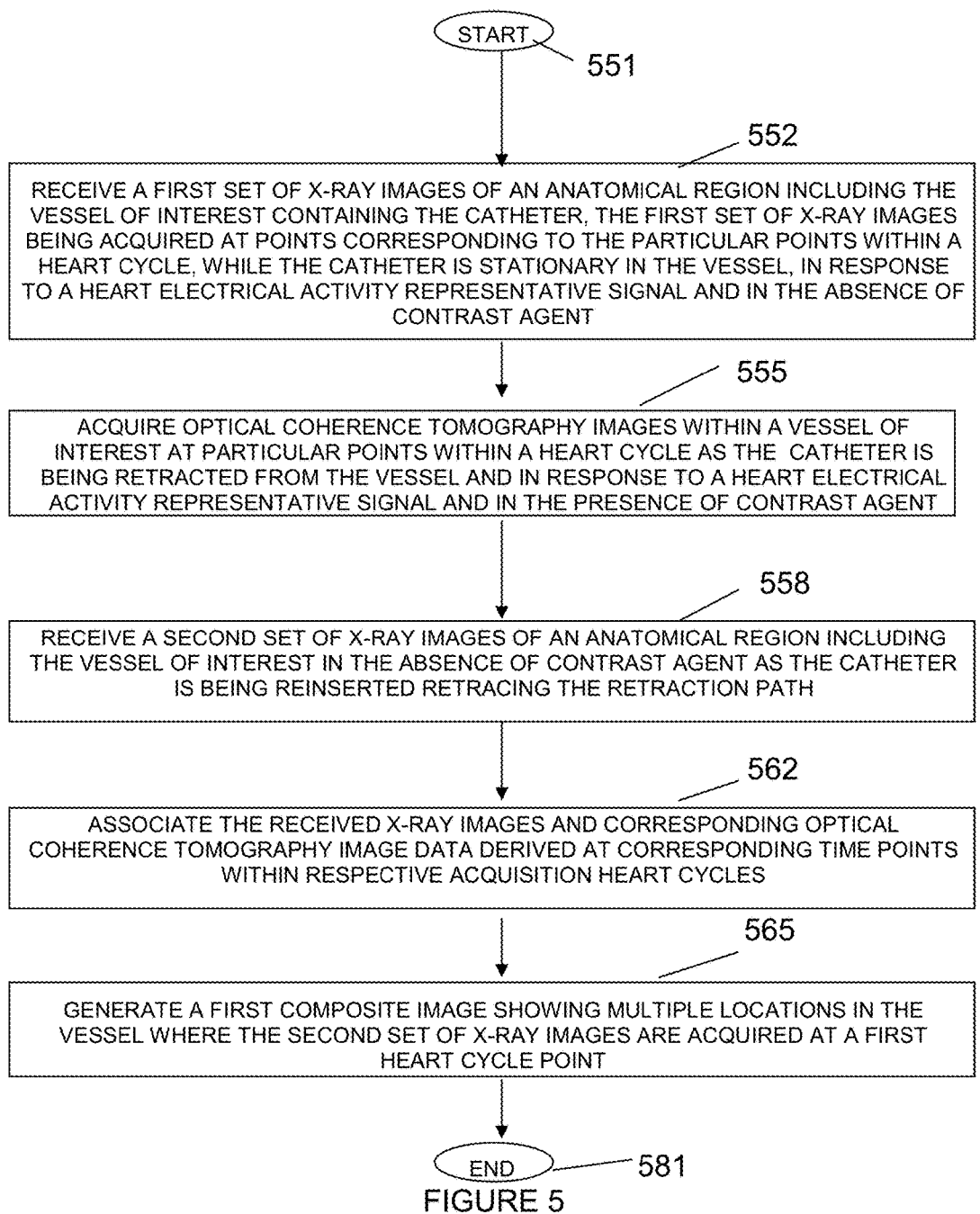
FIG. 5 shows a flowchart of a process used by a system for associating optical coherence tomography image data with X-ray image data, according to invention principles.

FIG. 5 shows a flowchart of a process used by system 10 (FIG. 1) for associating optical coherence tomography image data with X-ray image data. In step 552 following the start at step 551 X-ray imaging system interface 33 receives a first set of X-ray images of an anatomical region including the vessel of interest containing the catheter. In step 555 catheter 37 including lens 39, acquires optical coherence tomography images within the vessel of interest at particular points within a heart cycle as catheter 37 is being retracted from the vessel in the presence of contrast agent. In one embodiment, catheter 37 acquires optical coherence tomography images within the vessel of interest in response to a signal associated with completion of acquisition of the first set of X-ray images. The first set of X-ray images are acquired at points corresponding to the particular points within a heart cycle, while catheter 37 is stationary in the vessel, in response to a heart electrical activity representative signal and in the absence of contrast agent. Image data processor 15 generates a signal associated with completion of acquisition of the first set of X-ray images, for use in at least one of, (a) initiating automatic injection of contrast agent into a patient and (b) prompting a user to initiate automatic injection of contrast agent into a patient.

In step 558, X-ray imaging system interface 33 receives a second set of X-ray images of an anatomical region including the vessel of interest in the absence of contrast agent as catheter 37 is being reinserted retracing the retraction path. X-ray imaging system 25 acquires the second set of X-ray images synchronized with the retracement of the retraction path by catheter 37. Further, the second set of X-ray images comprises individual images acquired at intervals during retracement of the length of the retraction path to a reinserted position.

In step 562 image data processor 15 associates the received X-ray images and corresponding optical coherence tomography image data derived at corresponding time points within respective acquisition heart cycles. Image data processor 15 in step 565 generates a first composite image showing multiple locations in the vessel where the second set of X-ray images are acquired at a first heart cycle point. Image data processor 15 also generates a second composite image showing multiple locations in the vessel where the second set of X-ray images are acquired at a second heart cycle point. Processor 15 generates a display image showing the first and second composite images adjacent for comparison. Processor 15 generates a merged image comprising interleaved tracked points on the vessel identified based on distance from an initial position of the catheter tip. In one embodiment, the merged image comprises interleaved tracked points on the vessel using images acquired at a particular point in heart cycles. The merged image shown in FIG. 4 is an illustration of the mapping between the angiographic image and the time, which is also the horizontal axis of FIG. 2. The time is used to spatially correlate the angiographic image and the OCT image. It is this time mapping which permits system 10 to generate a visual output, which can be in the form of an image like FIG. 4 or a visualization of the spatial correlation between OCT image data and angiographic image data. The process of FIG. 5 terminates at step 581.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. A histogram of an image is a graph that plots the number of pixels (on the y-axis herein) in the image having a specific intensity value (on the x-axis herein) against the range of available intensity values. The resultant curve is useful in evaluating image content and can be used to process the image for improved display (e.g. enhancing contrast).

The system and processes of FIGS. 1-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system acquires OCT catheter images during one or more specific points in a cardiac cycle and acquires contrast-filled X-ray images to document a time duration encompassing injection of contrast agent for an OCT pullback and acquires images showing retracement of a pullback path of the OCT catheter without the presence of contrast agent but acquired at the same points of a cardiac cycle. Further, the processes and applications may, in alternative embodiments, be located on one or more (e.g., distributed) processing devices on a network linking the units FIG. 1. Any of the functions and steps provided in FIGS. 1-5 may be implemented in hardware, software or a combination of both. No claim element herein is to be construed under the provisions of 35 U.S.C. 112, sixth paragraph, unless the element is expressly recited using the phrase "means for."

What is claimed is:

1. A system comprising:
    a catheter including a lens, for acquiring a plurality of optical coherence tomography images within a vessel of interest as said catheter is being retracted through said vessel in the presence of contrast agent during a first pullback;
    an X-ray imaging system for acquiring a first plurality of X-ray images of said vessel of interest containing said catheter, as said catheter is being retracted through said vessel in the presence of contrast agent and during acquisition of the plurality of optical coherence tomography images, and for acquiring a second plurality of X-ray images of said vessel of interest containing said catheter, as said catheter is being retracted through said vessel in the absence of contrast agent during a second pullback, wherein the second pullback occurs after the first pullback to retrace a path of the catheter during the first pullback;
    a system and imaging control unit for moving said catheter more slowly during acquisition of the second plurality of X-ray images than during acquisition of the first plurality of X-ray images to acquire the catheter position; and
    an image data processor for:
        selecting X-ray images from the first plurality of X-ray images, indicating catheter shape by selecting X-ray images representative of a peak contrast agent concentration;
        tracking, from the first plurality of X-ray images, the vessel of interest with the catheter shape as indicated in the selected X-ray images;
        determining, for each of the second plurality of X-ray images, a location of the catheter by the tip of the catheter within said vessel;
        identifying one of the plurality of optical coherence tomography images as corresponding to the determined location of the catheter; and
        generating a composite image including the determined location of the catheter within the first plurality of X-ray images.

2. A system according to claim 1, wherein
    the plurality of said optical coherence tomography images, the first plurality of X-ray images, and the second plurality of X-ray images are acquired at R-wave peaks.

3. A system according to claim 1, wherein
    said image data processor generates a signal indicating completion of acquisition of said plurality of X-ray images of said vessel of interest containing said catheter, as said catheter is being retracted through said vessel in the absence of contrast agent, for use in at least one of, (a) initiating automatic injection of contrast agent into a patient and (b) prompting a user to initiate automatic injection of contrast agent into a patient.

4. A system according to claim 1, wherein
said image data processor identifies a second one of the plurality of optical coherence tomography images as corresponding to a second determined location of the catheter.

5. A system according to claim 4 wherein
said image data processor generates a composite image including the determined location and the second determined location of the catheter within one of the first plurality of X-ray images.

6. A system according to claim 1, wherein
the plurality of optical coherence tomography images, the first plurality of X-ray images, and the second plurality of X-ray images are acquired halfway between R-wave peaks.

7. A system according to claim 1, wherein the identified optical coherence tomography image corresponds to one of the first plurality of X-ray images that is representative of a peak contrast agent concentration.

8. A method comprising:
acquiring a plurality of optical coherence tomography images and a first plurality of X-ray images of a vessel of interest as a catheter is being retracted through said vessel in the presence of contrast agent during a first pullback;
selecting X-ray images from the first plurality of X-ray images, indicating catheter shape by selecting X-ray images representative of a peak contrast agent concentration;
tracking, from the first plurality of X-ray images, the vessel of interest with the catheter shape as indicated in the selected X-ray images;
acquiring a second plurality of X-ray images of said vessel of interest containing said catheter, as said catheter is being retracted through said vessel in the absence of contrast agent during a second pullback, wherein the second pullback occurs after the first pullback to retrace a path of the catheter during the first pullback, and wherein said catheter moves more slowly during acquisition of the second plurality of X-ray images than during acquisition of the first plurality of X-ray images to acquire the catheter position;
for each of the second plurality of X-ray images, determining a location of the catheter by the tip of the catheter within said vessel;
identifying one of the plurality of optical coherence tomography images as corresponding to the determined location of the catheter; and
generating a composite image including the determined location of the catheter within the first plurality of X-ray images.

9. A method according to claim 8, wherein
the plurality of optical coherence tomography images, the first plurality of X-ray images, and the second plurality of X-ray images are acquired at R-wave peaks.

10. A method according to claim 8, including the activity of
generating a signal indicating completion of acquisition of said plurality of X-ray images of said vessel of interest containing said catheter, as said catheter is being retracted through said vessel in the absence of contrast agent, for use in at least one of, (a) initiating automatic injection of contrast agent into a patient and (b) prompting a user to initiate injection of contrast agent into a patient.

11. A method according to claim 8, further comprising:
identifying a second one of the plurality of optical coherence tomography images corresponding to a second determined location of the catheter.

12. A method according to claim 11, further comprising:
generating a composite image including the determined location and the second determined location of the catheter within one of the first plurality of X-ray images.

13. A method according to claim 8, wherein the plurality of optical coherence tomography images, the first plurality of X-ray images, and the second plurality of X-ray images are acquired halfway between R-wave peaks.

* * * * *